United States Patent
Maiorino et al.

(10) Patent No.: US 11,653,911 B2
(45) Date of Patent: *May 23, 2023

(54) SYSTEM AND METHOD FOR MAKING TAPERED LOOPED SUTURE

(71) Applicant: Covidien LP, Mansfield, MA (US)

(72) Inventors: Nicholas Maiorino, Branford, CT (US); Timothy Kosa, Hamden, CT (US); Mark Buchter, Ansonia, CT (US); Keith Kroeber, Portland, CT (US); Richard C Hart, Saint Augustine, FL (US); Gary Suszynski, Woodbury, CT (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/564,477

(22) Filed: Dec. 29, 2021

(65) Prior Publication Data

US 2022/0117601 A1 Apr. 21, 2022

Related U.S. Application Data

(60) Continuation of application No. 16/706,888, filed on Dec. 9, 2019, now Pat. No. 11,224,420, which is a
(Continued)

(51) Int. Cl.
*B29C 65/08* (2006.01)
*A61B 17/06* (2006.01)
(Continued)

(52) U.S. Cl.
CPC ........ *A61B 17/06166* (2013.01); *B29C 65/08* (2013.01); *B29C 66/1122* (2013.01);
(Continued)

(58) Field of Classification Search
CPC .............. A61B 17/06166; B29C 65/08; B29C 66/1122; B29C 66/69; B29C 66/81431;
(Continued)

(56) References Cited

U.S. PATENT DOCUMENTS 2,514,184 A 7/1950 Lower
3,311,110 A 3/1967 Sol et al.
(Continued)

FOREIGN PATENT DOCUMENTS

EP 0444777 A1 9/1991
EP 0490143 A2 6/1992
(Continued)

OTHER PUBLICATIONS

Canadian Office Action issued in corresponding Canadian Application No. 2,699,826 dated Mar. 22, 2016.
(Continued)

*Primary Examiner* — James D Sells
(74) *Attorney, Agent, or Firm* — Carter, DeLuca & Farrell LLP

(57) ABSTRACT

An active anvil assembly for use in forming a looped suture is provided. The active anvil assembly includes an anvil member, a first sensor operably connected to the anvil member, and a control assembly. The first sensor is configured for measuring at least one of force, torque, and distance feedback. Also provided are systems and methods for forming a looped suture including an active anvil assembly.

18 Claims, 9 Drawing Sheets

Related U.S. Application Data continuation of application No. 16/426,269, filed on May 30, 2019, now Pat. No. 10,531,873, which is a continuation of application No. 15/689,066, filed on Aug. 29, 2017, now Pat. No. 10,314,576, which is a continuation of application No. 14/694,089, filed on Apr. 23, 2015, now Pat. No. 9,775,606, which is a division of application No. 13/480,614, filed on May 25, 2012, now Pat. No. 9,038,688, which is a continuation-in-part of application No. 13/051,544, filed on Mar. 18, 2011, now abandoned, which is a continuation-in-part of application No. 12/751,456, filed on Mar. 31, 2010, now Pat. No. 8,590,588.

(60) Provisional application No. 61/173,719, filed on Apr. 29, 2009.

(51) Int. Cl.
| | |
|---|---|
| *B29C 65/00* | (2006.01) |
| *A61B 17/00* | (2006.01) |
| *A61B 17/32* | (2006.01) |
| *B29L 31/00* | (2006.01) |

(52) U.S. Cl.
CPC ........ B29C 66/69 (2013.01); B29C 66/81431 (2013.01); B29C 66/8242 (2013.01); B29C 66/8322 (2013.01); B29C 66/9221 (2013.01); B29C 66/9261 (2013.01); B29C 66/961 (2013.01); *A61B 17/320068* (2013.01); *A61B 2017/00526* (2013.01); *A61B 2017/0619* (2013.01); *B29C 66/92211* (2013.01); *B29L 2031/753* (2013.01); *Y10T 156/1313* (2015.01); *Y10T 156/1378* (2015.01)

(58) Field of Classification Search
CPC ............ B29C 66/8242; B29C 66/8322; B29C 66/9221; B29C 66/9261; B29C 66/961; B29L 2031/753
USPC ...................................................... 156/580.1
See application file for complete search history.

(56) References Cited

U.S. PATENT DOCUMENTS

| | | | |
|---|---|---|---|
| 3,513,848 A | 5/1970 | Garvey | |
| 3,657,056 A | 4/1972 | Winston et al. | |
| 3,874,963 A | 4/1975 | Barger | |
| 4,575,372 A | 3/1986 | Gundersen | |
| 4,662,068 A | 5/1987 | Polonsky | |
| 4,950,285 A | 8/1990 | Wilk | |
| 5,059,212 A | 10/1991 | Korthoff | |
| 5,110,381 A | 5/1992 | Heckard et al. | |
| 5,226,535 A | 7/1993 | Rosdhy et al. | |
| 5,259,846 A | 11/1993 | Granger et al. | |
| 5,335,842 A | 8/1994 | Mostafazadeh | |
| 5,383,905 A | 1/1995 | Golds et al. | |
| 5,403,331 A | 4/1995 | Chesterfield et al. | |
| 5,417,700 A | 5/1995 | Egan | |
| 5,658,408 A | 8/1997 | Frantz et al. | |
| 5,746,856 A | 5/1998 | Hendershot et al. | |
| 5,772,814 A | 6/1998 | Grewell | |
| 5,820,011 A | 10/1998 | Ito et al. | |
| 5,865,836 A | 2/1999 | Miller | |
| 5,893,880 A | 4/1999 | Egan et al. | |
| 6,077,277 A | 6/2000 | Mollenauer et al. | |
| 6,089,438 A | 7/2000 | Suzuki et al. | |
| 6,174,324 B1 | 1/2001 | Egan et al. | |
| 6,217,591 B1 | 4/2001 | Egan et al. | |
| 6,286,746 B1 | 9/2001 | Egan et al. | |
| 6,296,659 B1 | 10/2001 | Foerster | |
| 6,358,271 B1 | 3/2002 | Egan et al. | |
| 6,368,343 B1 | 4/2002 | Bonutti et al. | |
| 6,409,743 B1 | 6/2002 | Fenton, Jr. | |
| 6,423,088 B1 | 7/2002 | Fenton, Jr. | |
| 6,488,690 B1 | 12/2002 | Morris et al. | |
| 6,669,705 B2 | 12/2003 | Westhaver et al. | |
| 6,749,704 B2 | 6/2004 | Boussu et al. | |
| 6,767,426 B1 | 7/2004 | Yamamoto | |
| 6,797,088 B2 | 9/2004 | Solinski | |
| 7,090,111 B2 | 8/2006 | Egan et al. | |
| 7,429,266 B2 | 9/2008 | Bonutti et al. | |
| 7,438,210 B2 | 10/2008 | Gale et al. | |
| 7,533,791 B2 | 5/2009 | Steiner et al. | |
| 7,582,097 B2 | 9/2009 | McRury et al. | |
| 7,611,039 B2 | 11/2009 | Hesse et al. | |
| 7,758,614 B2 | 7/2010 | Fenton et al. | |
| 7,775,413 B2 | 8/2010 | Oblak et al. | |
| 7,776,171 B2 | 8/2010 | Lehto et al. | |
| 7,810,541 B2 | 10/2010 | Wild et al. | |
| 7,819,158 B2 | 10/2010 | Klinstein et al. | |
| 8,056,599 B2 | 11/2011 | Maiorino et al. | |
| 8,403,017 B2 | 3/2013 | Maiorino et al. | |
| 8,590,588 B2 | 11/2013 | Maiorino et al. | |
| 8,968,362 B2 | 3/2015 | Thomas | |
| 9,038,688 B2 | 5/2015 | Maiorino et al. | |
| 9,775,606 B2 | 10/2017 | Maiorino et al. | |
| 10,314,576 B2 | 6/2019 | Maiorino et al. | |
| 10,531,873 B2 | 1/2020 | Maiorino et al. | |
| 11,224,420 B2 | 1/2022 | Maiorino et al. | |
| 2002/0011508 A1 | 1/2002 | Egan et al. | |
| 2002/0029065 A1 | 3/2002 | Shchervinsky | |
| 2002/0116027 A1 | 8/2002 | Egan et al. | |
| 2003/0111157 A1 | 6/2003 | Ehlert et al. | |
| 2004/0112547 A1 | 6/2004 | Tamamoto | |
| 2004/0122451 A1 | 6/2004 | Wood | |
| 2005/0165448 A1 | 7/2005 | Egan et al. | |
| 2005/0216058 A1 | 9/2005 | Egan et al. | |
| 2005/0241143 A1 | 11/2005 | Mizuno et al. | |
| 2006/0025858 A1 | 2/2006 | Alameddine | |
| 2006/0144902 A1 | 7/2006 | Pochardt et al. | |
| 2006/0149485 A1 | 7/2006 | Oblak et al. | |
| 2006/0259076 A1 | 11/2006 | Burkhart et al. | |
| 2007/0119535 A1 | 5/2007 | Watanabe | |
| 2007/0251643 A1* | 11/2007 | Umebayashi ..... B29C 66/92613 156/350 |
| 2008/0105385 A1 | 5/2008 | Wild et al. | |
| 2008/0110550 A1 | 5/2008 | Lehto et al. | |
| 2009/0133803 A1 | 5/2009 | Lehto | |
| 2009/0216269 A1 | 8/2009 | Harrington et al. | |
| 2009/0248070 A1 | 10/2009 | Kosa et al. | |
| 2009/0250171 A1 | 10/2009 | Wieduwilt et al. | |
| 2009/0259251 A1 | 10/2009 | Cohen | |
| 2010/0024956 A1 | 2/2010 | Vogler | |
| 2010/0043939 A1 | 2/2010 | Heinimann et al. | |
| 2010/0101707 A1 | 4/2010 | Maiorino et al. | |
| 2010/0276061 A1 | 11/2010 | Oblak et al. | |
| 2011/0180196 A1 | 7/2011 | Hart et al. | |
| 2012/0024482 A1 | 2/2012 | Maiorino et al. | |

FOREIGN PATENT DOCUMENTS

| | | |
|---|---|---|
| EP | 2814157 A2 | 12/2014 |
| FR | 2729940 A1 | 8/1996 |
| WO | 9625109 A1 | 8/1996 |
| WO | 9926542 A1 | 6/1999 |
| WO | 0030550 A1 | 6/2000 |
| WO | 0222025 A1 | 3/2002 |
| WO | 2005087113 A1 | 9/2005 |

OTHER PUBLICATIONS

European Search Report EP 12195006.7.-2310 dated Jan. 30, 2013.
European Search Report EP 10 25 0847 dated Aug. 25, 2010.
European Search Report EP 10 25 1270 dated Feb. 8, 2012.
European Search Report EP 12163323.4 dated Jul. 25, 2012.
International Search Report PCT/US2013/042340 dated Aug. 27, 2013.
Supplementary European Search Report dated Jan. 14, 2016 in corresponding European Patent Application No. 13793791, 8 pages.

(56) References Cited

OTHER PUBLICATIONS

European Office Action dated Mar. 28, 2017, issued in EP Application No. 13793791.
European Office Action dated Feb. 17, 2020, issued in EP Appln. No. 13793791.

* cited by examiner

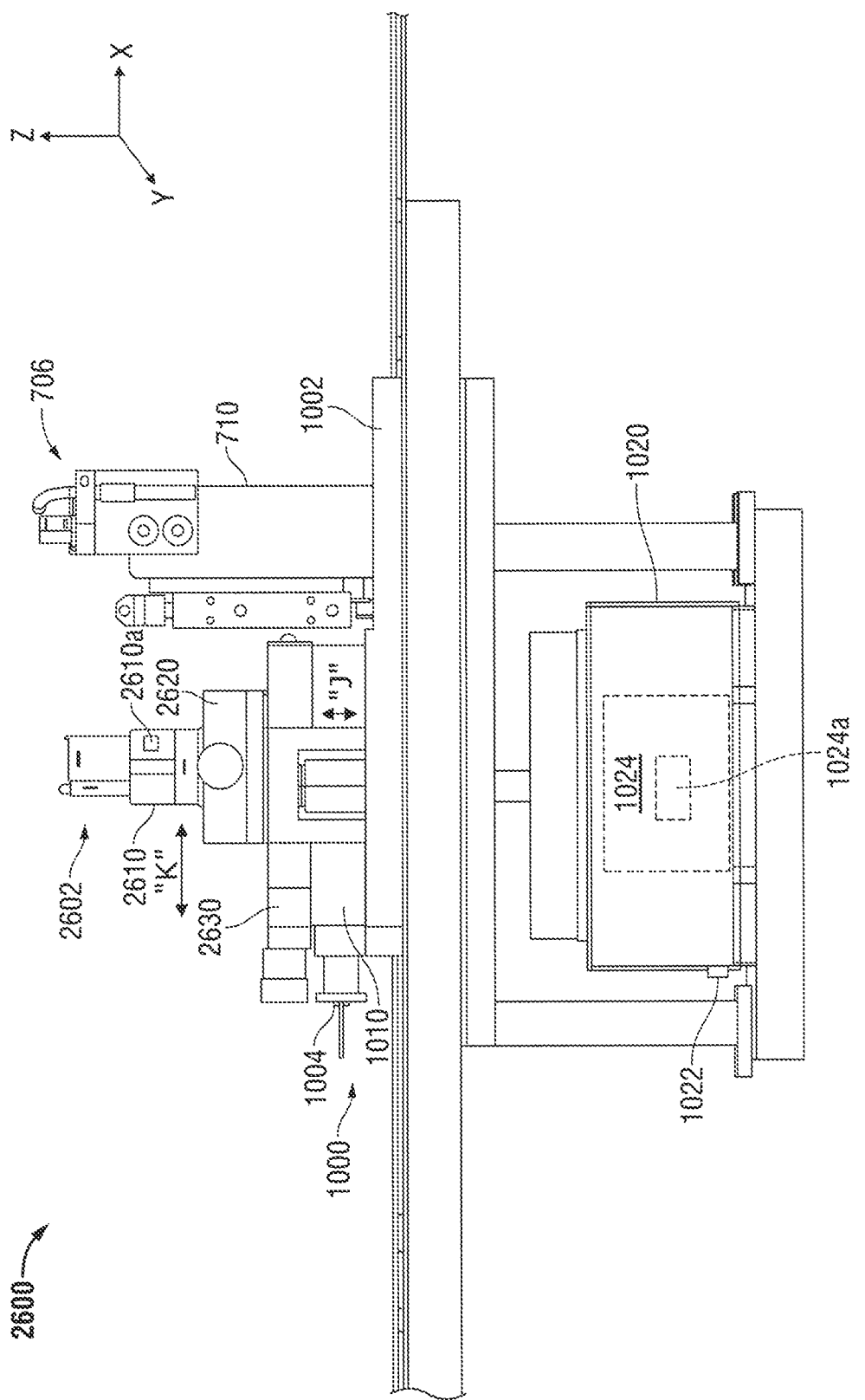

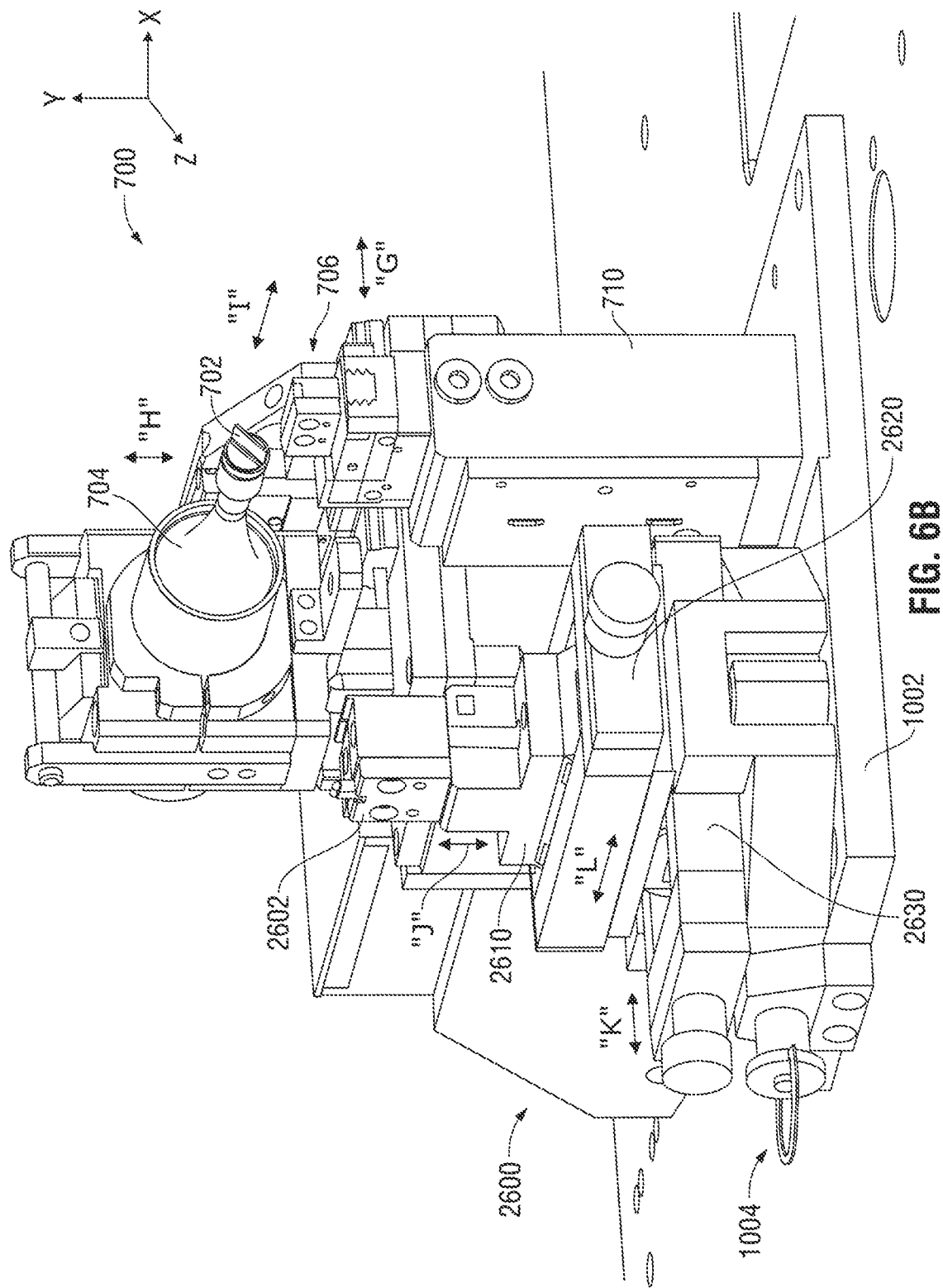

SYSTEM AND METHOD FOR MAKING TAPERED LOOPED SUTURE

CROSS-REFERENCE TO RELATED APPLICATIONS

This application is a continuation of U.S. patent application Ser. No. 16/706,888, filed Dec. 9, 2019, which is a continuation of U.S. patent application Ser. No. 16/426,269, filed May 30, 2019, now U.S. Pat. No. 10,531,873, which is a continuation of U.S. patent application Ser. No. 15/689,066, filed Aug. 29, 2017, now U.S. Pat. No. 10,314,576, which is a continuation of U.S. patent application Ser. No. 14/694,089, filed Apr. 23, 2015, now U.S. Pat. No. 9,775,606, which is a divisional of U.S. patent application Ser. No. 13/480,614 filed May 25, 2012, now U.S. Pat. No. 9,038,688, which is a continuation-in-part of U.S. patent application Ser. No. 13/051,544, filed Mar. 18, 2011, now abandoned, which is a continuation-in-part of U.S. patent application Ser. No. 12/751,456, filed Mar. 31, 2010, now U.S. Pat. No. 8,590,588, which claims benefit of and priority to U.S. Provisional Application Ser. No. 61/173,719, filed Apr. 29, 2009, the disclosures of which are incorporated by reference herein in their entirety.

BACKGROUND

Technical Field

The present disclosure relates to a system of forming a looped suture. More particularly, the present disclosure relates to an automated system of forming a looped suture having a tapered cut.

Background of Related Art

The forming of a loop in a suture is known, as are methods of forming the loop. A loop may be formed in a suture for a number of reasons. For example, during manufacture a loop may be formed in the suture to assist in further processing of the suture, e.g., for holding the suture as barbs are formed along the length thereof. Alternatively, a loop formed in a suture during manufacture may be used to secure the suture to tissue. In this manner, once the non-looped end of the suture is inserted through tissue, that end may be threaded through the loop to form a slip knot-like configuration that may be tied to secure tissue. In another application, a loop may be formed in a suture in place of a knot. This requires the use of a handheld instrument that may be brought into an operating room.

Therefore, it would be beneficial to have a system and method of forming a looped suture to include a taper cut.

SUMMARY

Accordingly, an active anvil assembly for use in forming a looped suture is disclosed. The active anvil assembly includes an anvil member, a first sensor operably connected to the anvil member, and a control assembly. The first sensor is configured for providing force feedback. The anvil member may be configured to operate with an ultrasonic welding horn to join a first length of a thread and a second length of the thread to form a loop in the thread. In particular, the loop may be formed at the distal end of the thread. In one embodiment, the anvil member includes a channel configured to selectively receive at least a portion of a first length of a thread.

The control assembly includes a motor which may be configured to move a mounting member in relation to the ultrasonic welding horn. The control assembly may be configured to vertically move the anvil member. In certain embodiments, the mounting member is configured to move the anvil member. The anvil member may be selectively movable in at least first and second directions relative to the ultrasonic welding horn. Further, the control assembly may be configured to move the mounting member in relation to a mounting base. The anvil member may be configured for approximation towards and away from the ultrasonic welding horn. The active anvil assembly may further include a first adjustable stage configured to translate laterally relative to the ultrasonic welding horn and/or a second adjustable stage configured to translate forwards and backwards relative to the ultrasonic welding horn.

Also disclosed is system for forming a looped suture. The system includes an active anvil assembly configured for retaining the suture during welding of the loop and a trimming assembly for removing excess thread from the loop in the thread. The active anvil assembly includes an anvil member operably connected to a first sensor and a control assembly configured for movement of the anvil member. The system may further include one or more of a flipper gripping assembly configured for creating a loop in the thread, a carriage assembly configured for advancing the thread through the loop forming process, a cutter assembly for severing the thread upon completion of the loop forming process, a thread lengthening assembly configured for extending the length of the thread, and a monitoring assembly configured for monitoring the forming process.

Additionally, a method of forming a looped suture is disclosed. The method includes the step of providing a system including a welding assembly and a trimming assembly, wherein the welding assembly includes an ultrasonic welding horn and an active anvil assembly. The method further includes the steps of receiving a first length of thread adjacent a second length of thread between the ultrasonic welding horn and the active anvil assembly, approximating at least one of an anvil member of the active anvil assembly and the ultrasonic welding horn towards the other, activating the ultrasonic welding horn, joining the adjacent first and second lengths of thread, and approximating at least one of the anvil member and the ultrasonic welding horn away from the other of the ultrasonic welding horn and anvil member.

In one of the disclosed methods, at least one of the anvil member and the ultrasonic welding horn is approximated towards the other of the ultrasonic welding horn and anvil member until a predefined torque value is sensed by a sensor disposed in the active anvil assembly. In a second embodiment, at least one of the anvil member and the ultrasonic welding horn is approximated towards the other of the ultrasonic welding horn and anvil member until a predefined force value is sensed by a sensor disposed in the active anvil assembly. In a third embodiment, at least one of the anvil member and the ultrasonic welding horn is approximated towards the other of the ultrasonic welding horn and anvil member as predefined distance is sensed. In a fourth embodiment, the anvil member and the ultrasonic welding horn is approximated towards the other of the ultrasonic welding horn and anvil member as a predefined force value is sensed.

The method of forming a looped suture may further include the steps of operably engaging the joined first and second lengths of thread with a gripping anvil of the trimming assembly, approximating at least one of the gripping anvil and an ultrasonic cutter towards the other of the ultrasonic cutter and the gripping anvil, removing excess thread from the joined first and second lengths of thread, and approximating the gripping anvil away from the ultrasonic cutter.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 6A is an enlarged side view of embodiments of portions of the welding assembly and the trimming assembly of FIG. 2;

FIG. 6B is a perspective view of portions of the active anvil assembly and trimming assembly of FIG. 4;

DETAILED DESCRIPTION

Figure 1A:
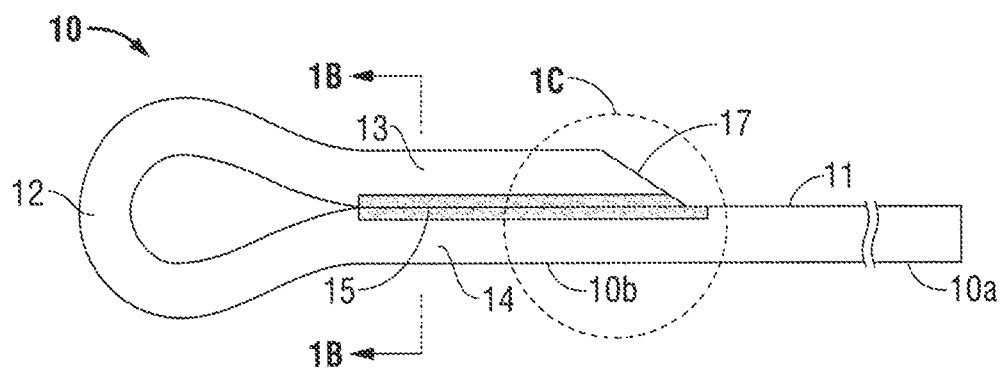
FIG. 1A is a side view of a looped suture including a tapered portion.

A system and method for forming a looped suture including a tapered cut is described herein. Referring initially to FIG. 1A, a looped suture formed in accordance with the method of the present disclosure is shown generally as looped suture 10. Suture 10 is formed from a monofilament thread 11, however, it is envisioned that suture 10 may include braided threads, multifilament threads and other surgical fibers. Although shown having a circular cross-sectional geometry, the cross-sectional geometry of thread 11 may be of any suitable shape. For example, thread 11 may be round, elliptical, square, flat, triangular, octagonal, and rectangular. Thread 11 may be formed of degradable materials, non-degradable materials, and combinations thereof. Thread 11 may be formed using any technique within the purview of those skilled in the art, such as, for example, extrusion, molding and/or solvent casting.

Figure 1B:
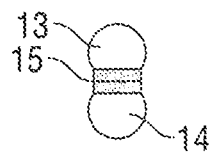
FIG. 1B is a cross-sectional end view of the looped suture of FIG. 1B, taken along line 1B-1B.
Figure 1C:
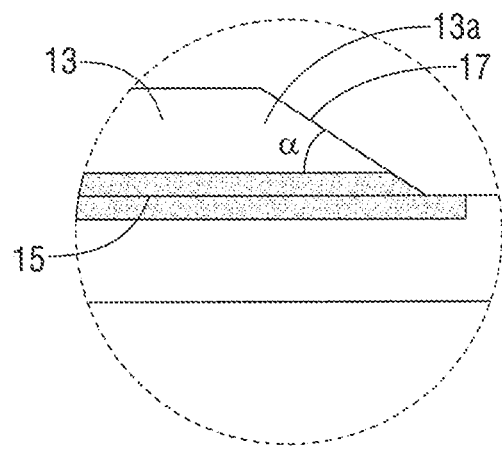
FIG. 1C is an enlarged side view of FIG. 1A.

With reference to FIGS. 1A-1C, looped suture 10 includes a loop 12 formed on a distal end 10b of the suture 10. Loop 12 forms a substantially teardrop shape and may be formed of any size. Although a substantially teardrop-shaped loop 12 is illustrated, other variations, such as circular, oval and spherical-shaped loops are envisioned. A first section 13 of monofilament thread 11 overlays a second section 14 of thread 11 to form loop 12. The adjacent surfaces of first and second sections 13, 14 form a joined segment or joint 15. As shown, joined segment 15 extends beyond first section 13 of thread 11. In this manner, first and second sections 13, 14 of thread 11 are less likely to separate or peel away from each other as looped suture 10 is pulled through tissue (not shown).

As will be described in further detail below, first and second sections 13, 14 of thread 11 are welded together to form joined section 15. In this manner, first and second sections 13, 14 of thread 11 are locally heated until each fuses to form joined segment 15. Various types of energy may be used to locally heat first and second sections 13, 14 to form joined segment 15, including, radiofrequency (RF), ultrasonic, laser, electrical arc discharge, and thermal. Alternatively, first and second sections 13, 14 of thread 11 may be joined using glue, epoxy or other adhesive.

With particular reference to FIG. 1C, a proximal end 13a of first section 13 is angled to form a tapered surface 17. Tapered surface 17 angles downwardly towards proximal end 10a (FIG. 1A) of looped suture 10. Tapered surface 17 may form an angle between zero degrees (0°) and ninety degrees (90°), and preferably between about fifteen degrees (15°) to about sixty degrees (60°). Tapered surface 17 facilitates insertion of loop 12 into or through tissue. Tapered surface 17 may be formed prior to, during or following the joining of first and second sections 13, 14.

Although shown having a substantially planar taper, tapered surface 17 may include any number of configurations. For example, tapered surface 17 may be beveled, may include a laterally and longitudinally concave taper, may include a laterally and longitudinally convex taper, or may include any combination thereof. Tapered surface 17 may be selected depending on the tissue being sutured and/or the depth loop 12 is desired to be received within the tissue.

Figure 2:
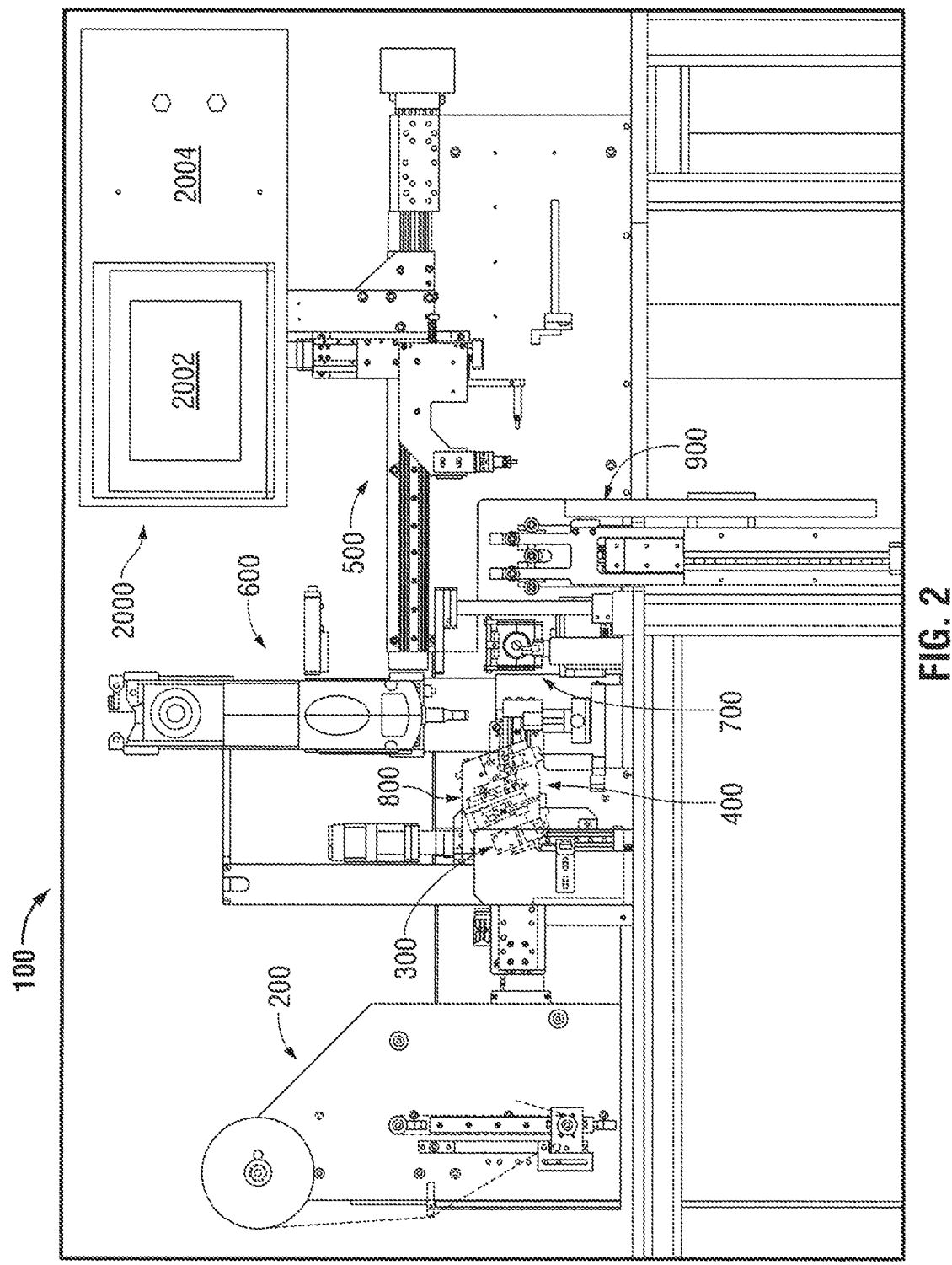
FIG. 2 is a side view of a tapered loop forming system of the present disclosure.

A system for forming loop 12 on distal end 10b of looped suture 10 will now be described with reference to FIGS. 2-7B, and is shown generally as tapered loop forming system 100. Although shown as being automated, it is envisioned that various components and/or process within tapered loop forming system 100 may manually completed. Referring initially to FIG. 2, system 100 includes a suture supply assembly 200, an initial gripping assembly 300, a flipper gripping assembly 400, a carriage assembly 500, a welding assembly 600, a trimming assembly 700, a cutter assembly 800, and may optionally include a thread lengthening assembly 900 and a monitoring assembly 2000.

Figure 3:
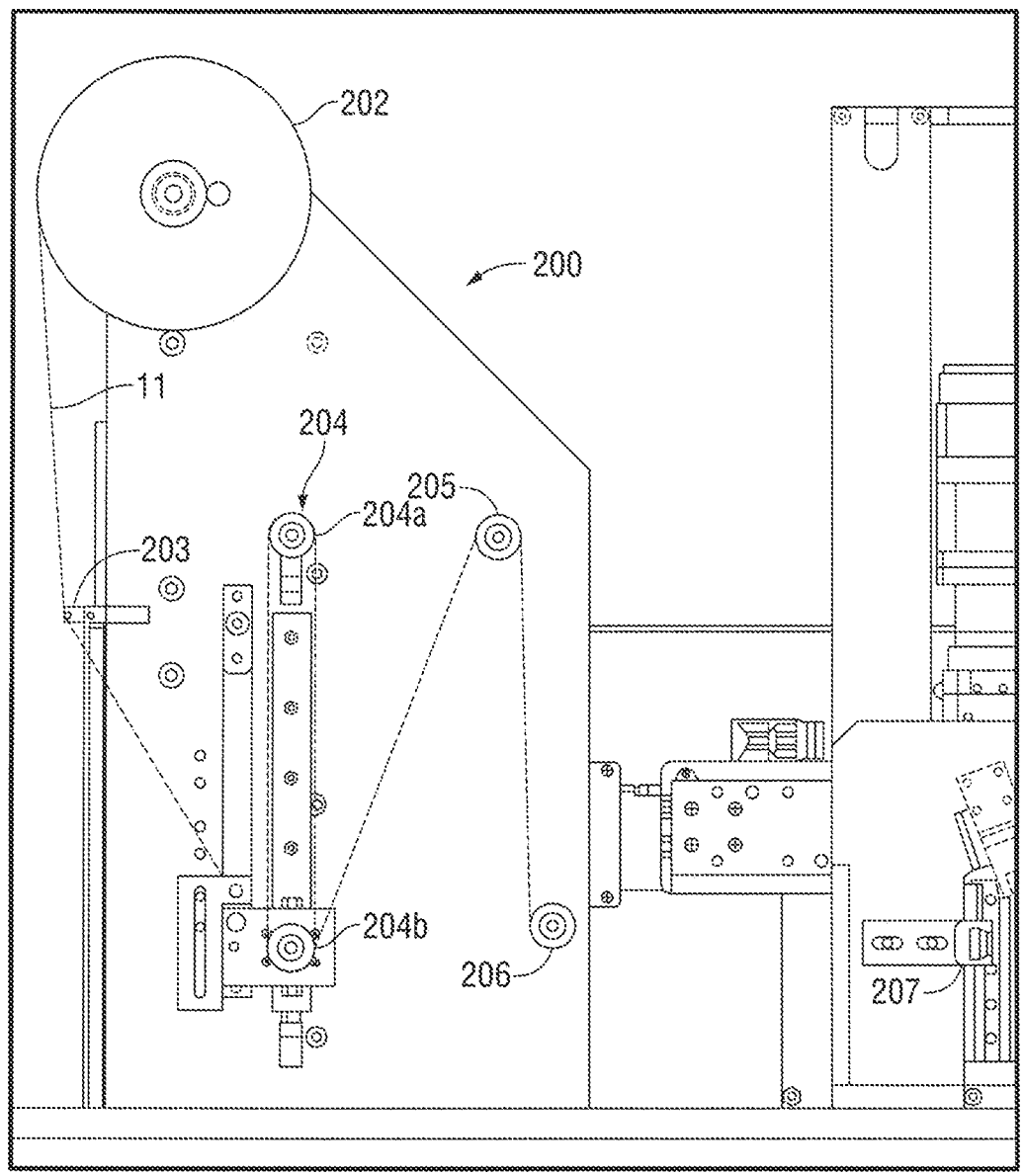
FIG. 3 is an enlarged side view of a suture supply assembly of the tapered loop forming system of FIG. 2.

With reference now to FIG. 3, supply assembly 200 is configured to provide thread 11 to initial gripping assembly 300. Supply assembly 200 includes a spool 202, a first guide member 203, a roller assembly 204, first and second rollers 205, 206 and a second guide member 207. First guide member 203 is configured to direct thread 11 from spool 202 to roller assembly 204. Roller assembly 204 includes a set of fixed rollers 204a and a set of adjustable rollers 204b. Roller assembly 204 is configured to receive thread 11 about fixed and adjustable rollers 204a, 204b a plurality of times. As shown, rollers 204a, 204b are configured to receive thread 11 thereabout four (4) times, however, roller assembly 204 may be configured to receive thread 11 thereabout more or less than four times. First and second rollers 205, 206 are positioned to direct thread 11 through second guide member 207. Although shown including supply assembly 200 for providing a continuous supply of thread 11 from spool 202, alternative supply assemblies are known and may be modified for use with system 100. For example, thread 11 may be provided in fixed or predetermined lengths rather than continuously from a spool. In this manner, the aspects of the present disclosure should not be read as limited to the supply assembly herein disclosed.

Figure 4:
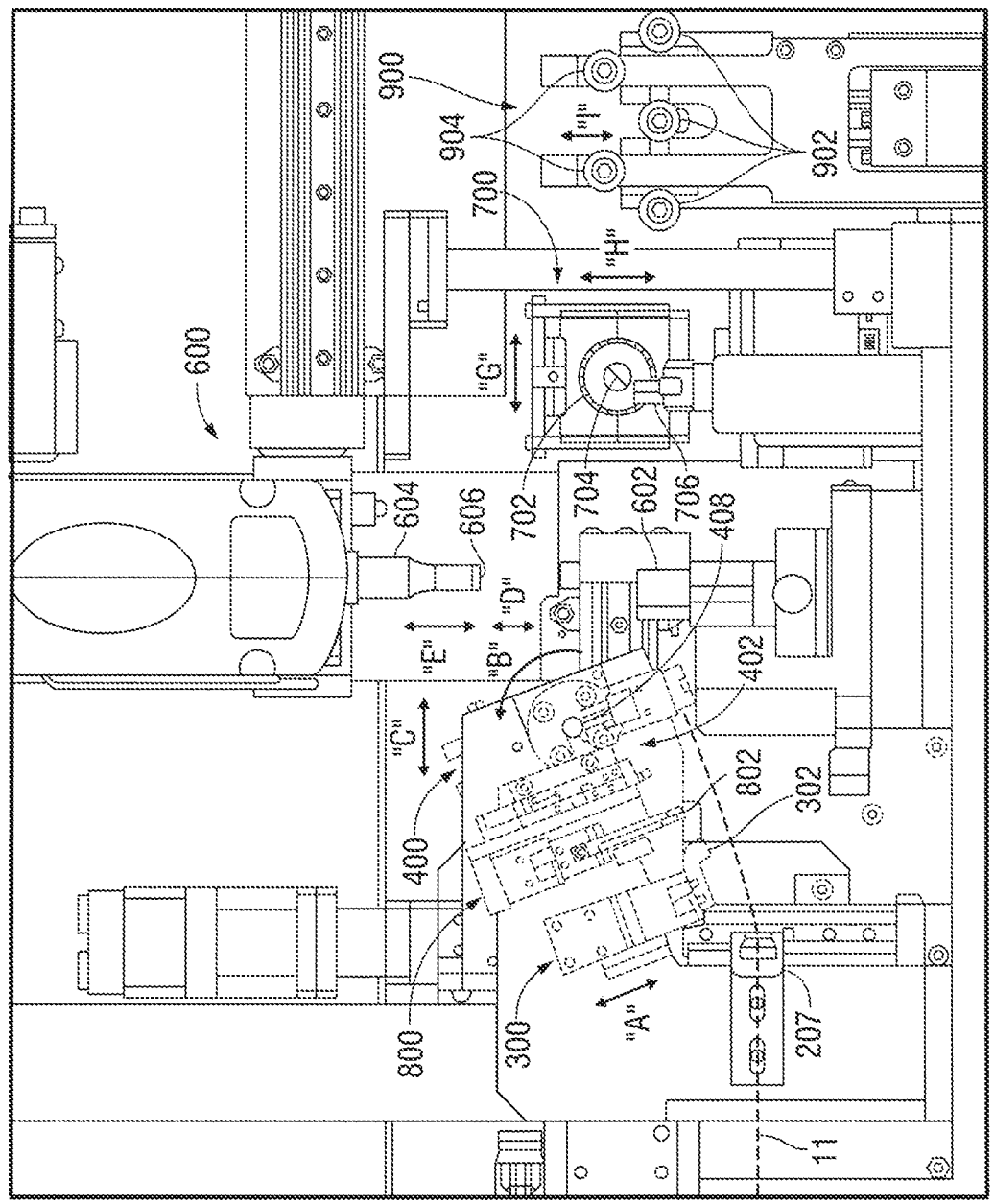
FIG. 4 is an enlarged sectional side view of the tapered loop forming system of FIG. 2.

Turning now to FIG. 4, initial gripping assembly 300 includes an initial gripper 302 configured to selectively engage and selectively grasp thread 11 throughout the loop end forming process. Initial gripping assembly 300 translates on a diagonal, in the direction of arrows "A". During the looped end forming process, initial gripping assembly 300 is activated to grasp a proximal end of thread 11 when tension is applied to a distal end of thread 11 to prevent excess thread from being pulled from supply assembly 200. In this manner, initial gripping assembly 300 may include any device or apparatus capable of selectively grasping thread 11.

Figure 5:
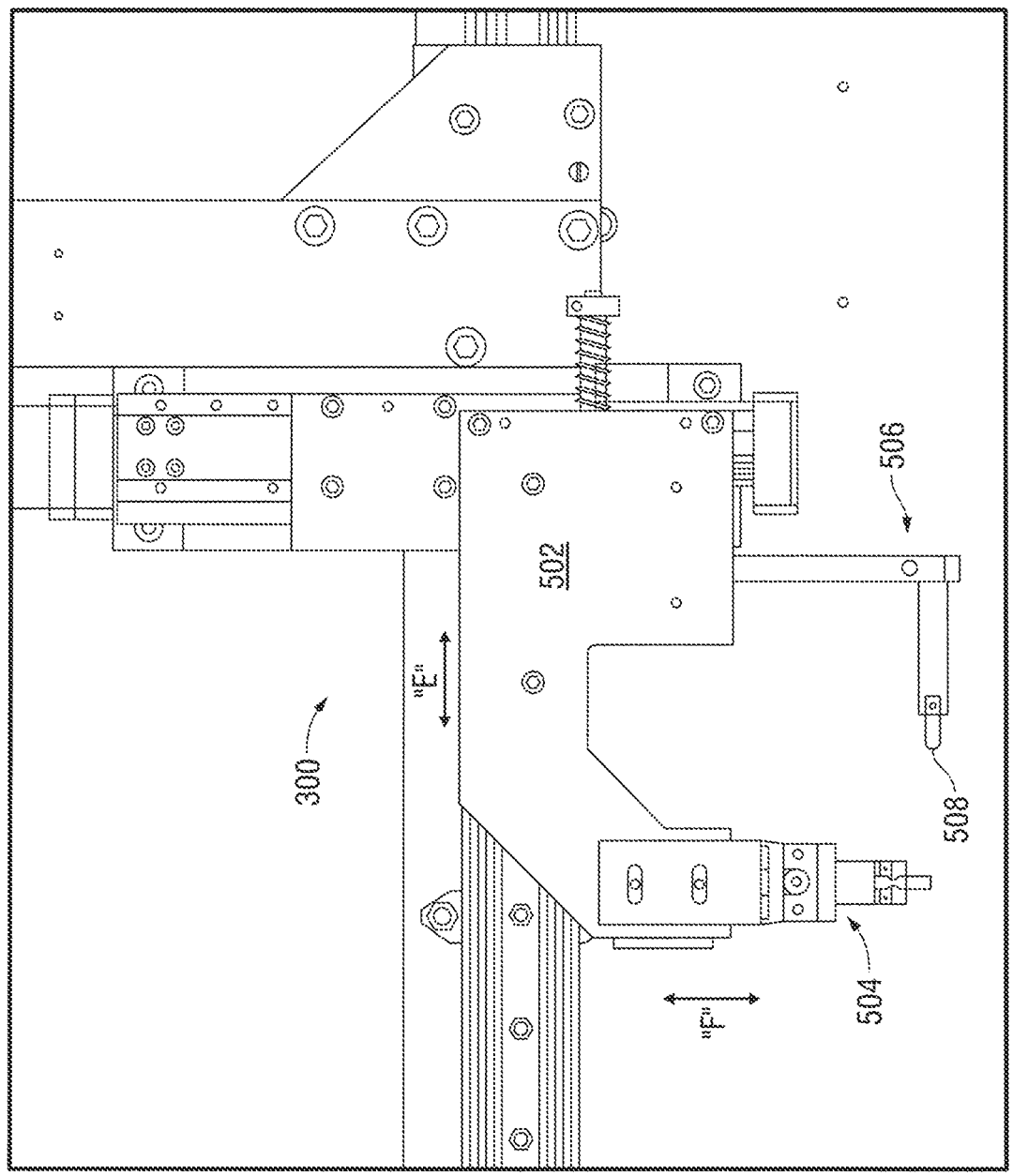
FIG. 5 is an enlarged side view of carriage assembly of the tapered loop forming system of FIG. 2.

With reference still to FIG. 4, flipper gripping assembly 400 is configured to create loop 12 in thread 11. Gripping assembly 400 includes a rotating gripper 402 configured to selectively grasp a first end of thread 11. A mandrel 408 extends from rotating gripper 402 and includes a slot (not shown) configured to receive a hook 508 from carriage assembly 500 (FIG. 5). Rotating gripper 402 is configured to rotate relative to mandrel 408, in the direction of arrow "B", to loop thread 11 around mandrel 408. Flipper gripping assembly 400 is configured to move horizontally, in the direction of arrows "C", and vertically, in the direction of arrows "D".

With reference now to FIG. 5, carriage assembly 500 is configured to translate thread 11 through the loop forming process. Carriage assembly 500 includes a support member 502 having a tag end gripper 504 and a hook assembly 506. A hook 508 extends from hook assembly 506 and is configured to receive thread 11 thereabout. Carriage assembly 500 optionally includes a tensioning cylinder (not shown) for tensioning thread 11 with a predetermined force to test the strength of weld 15 (FIG. 1B). Carriage assembly 500 is configured to move horizontally, in the direction of arrows "E", and vertically, in the direction of arrows "F".

With reference to FIGS. 4 and 6A-6C, welding assembly 600 is configured to weld joined segment 15 in thread 11 to form loop 12 (FIG. 1A). Welding assembly 600 includes an active anvil assembly 2600 configured for selective engagement with an ultrasonic welding horn 604. In one embodiment, ultrasonic welding horn 604 may be manufactured by Branson Ultrasonics Corporation (Danbury, Conn.). The term ultrasonic as used herein includes high frequency vibrations which are applied to workpieces being held together to create a solid state weld. Further, it should be understood that the term "welding horn" as used herein includes any component which transmits the mechanical vibrations (of a converted electrical signal) to the parts to be welded, e.g., a thread or suture. Active anvil assembly 2600 includes an anvil member 2602, a first sensor 2610a and a control assembly 1020.

Figure 7A:
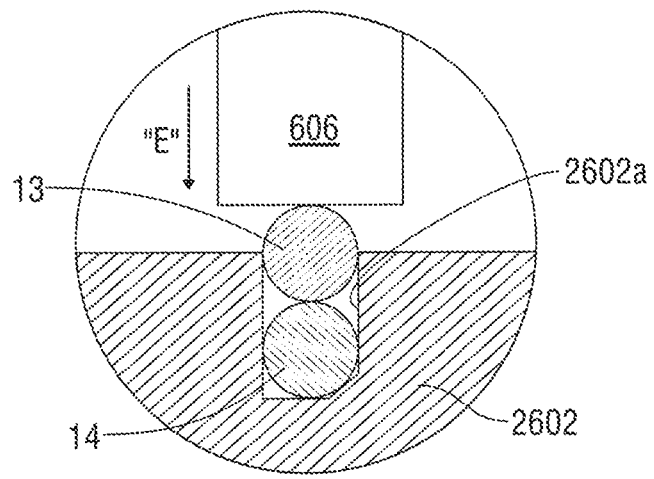
FIG. 7A is an enlarged cross-sectional side view of welding assembly of the loop forming system of FIG. 2, in a partially activated position.
Figure 7B:
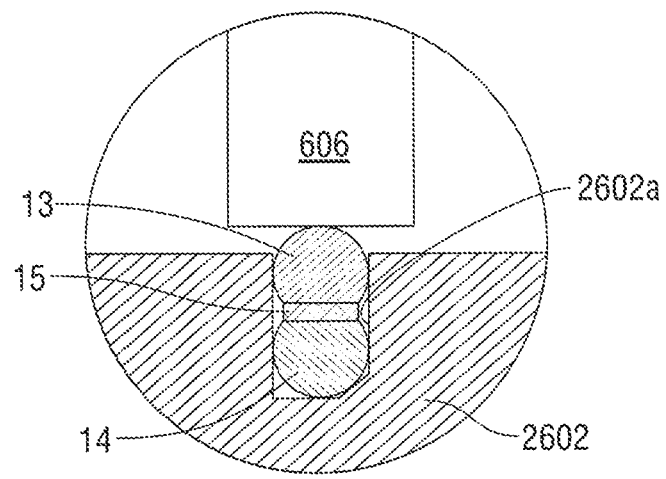
FIG. 7B is an enlarged cross-sectional side view of the welding assembly of FIG. 7A, in a fully activated position.

With reference to FIGS. 7A and 7B, ultrasonic welding horn 604 includes a flat die 606 configured to engage first section 13 of thread 11 during the welding step. As shown, anvil member 2602 defines a channel 2602a configured to receive the entire width of second section 14 and more than half the width of first section 13 of thread 11. In an alternative embodiment, flat die 606 may include a channel or recess (not shown) for receiving at least a portion of first section 13 of thread 11 instead of or in addition to the channel 2602a in the anvil member 2602.

Figure 6C:
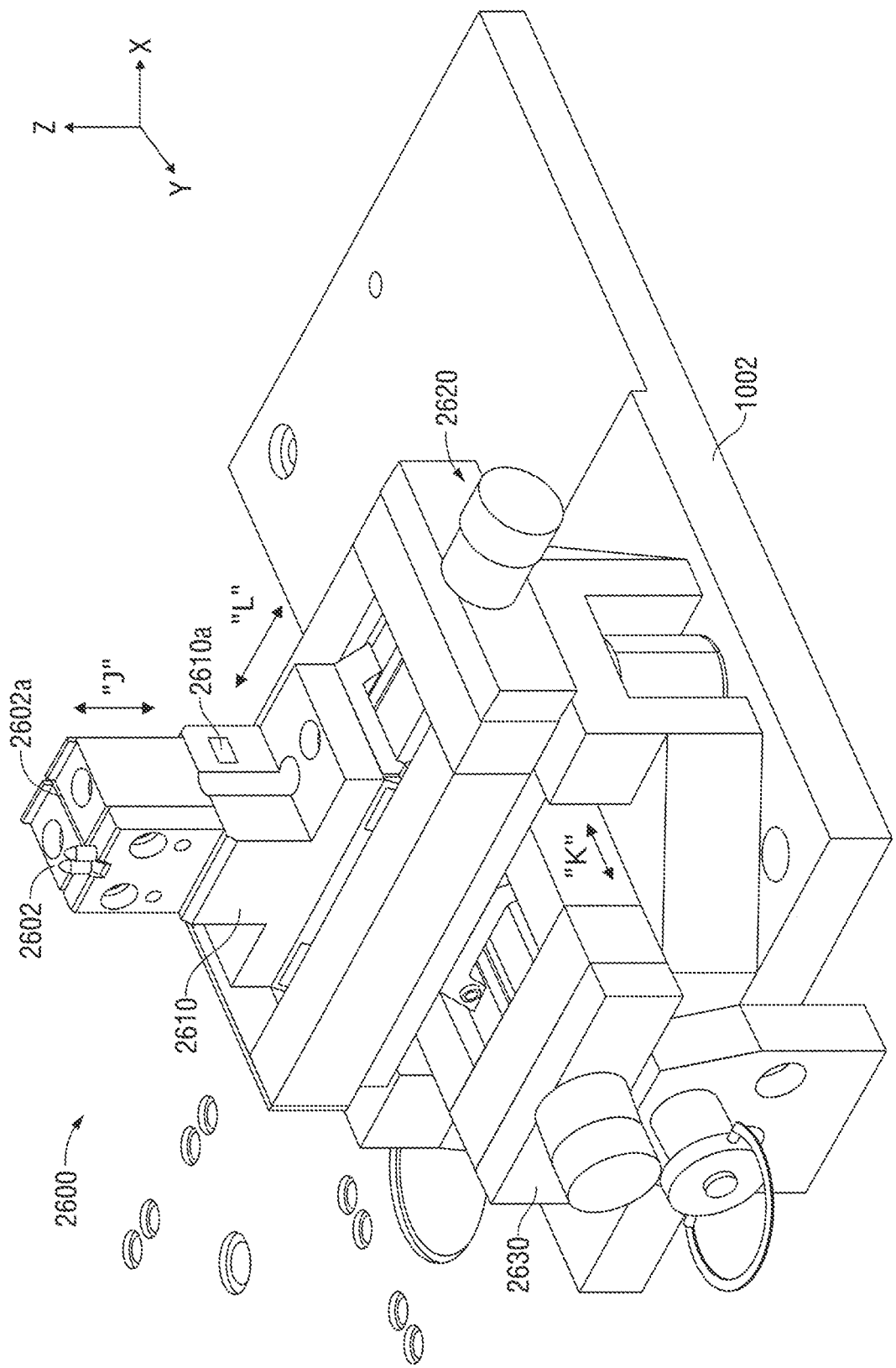
FIG. 6C is a perspective view of portions of the active anvil assembly of FIGS. 6A and 6B.

Turning to FIGS. 6A-6C, the active anvil assembly 2600 will be described in greater detail. As described hereinabove, the active anvil assembly 2600 includes an anvil member 2602 and a first sensor 2610a which is operably connected to the anvil member 2602. The first sensor 2610a is incorporated within the anvil base 2610 and the first sensor 2610a interacts with and provides feedback to a control assembly 1020 (later described), effecting movement of the active anvil assembly 2600 during the loop forming process. First sensor 2610a is operably connected to the anvil member 2602 and may be configured to measure force, torque, distance and/or other conditions within active anvil assembly 2600. In particular, first sensor 2610a is configured to provide force feedback to active anvil assembly 2600. First sensor 2610a is disposed above first and second adjustable stages, 2620 and 2630, respectively. Either or both of anvil member 2602 and adjustable stages 2620, 2630, may be configured for movement in one or more directions prior to, during, or following the respective joining and trimming processes.

With particular reference to FIG. 6B, anvil base 2610 operably engages first adjustable stage 2620 and is configured to be selectively positioned relative thereto, as indicated by arrows "L." As shown in the drawings, first adjustable stage 2620 is configured to move the anvil base 2610 in a forward/backward or front/back direction. First adjustable stage 2620 operably engages second adjustable stage 2630 and is configured to be selectively positioned relative thereto, as indicated by arrows "K." As shown in drawings, second adjustable stage 2630 is configured to move anvil base 2610 in a lateral or side to side direction. Second adjustable stage 2630 operably engages a mounting member 1010 of mounting assembly 1000. It should be noted that although the adjustable stages 2620 and 2630 provided herein are described as part of the active anvil assembly 2600, it is envisioned that the adjustable stages 2620 and 2630 may be provided as separate assemblies and/or may operate separately from anvil member 2602 and anvil base 2610.

With particular reference to FIG. 6A, the active anvil assembly 2600 further includes a mounting assembly 1000. Mounting assembly 1000 includes a mounting base 1002, mounting member 1010, and control assembly 1020. The mounting member 1010 is configured to further move the anvil member 2602. In particular, mounting member 1010 is operably engaged with mounting base 1002 and is configured to be raised and lowered relative to mounting base 1002, as indicated by arrows "J" to raise and lower anvil member 2602 relative to ultrasonic welding horn 604. As shown, mounting member 1010 is moved relative to mounting base 1002 by a control assembly 1020. A locking pin 1004 is configured for selective engagement with mounting member 1010. In particular, the locking pin 1004 is configured to prevent movement of mounting member 1010 relative to mounting base 1002.

Control assembly 1020 includes a motor 1024 that is configured to cause the raising and lowering, in other words, the vertical movement of mounting member 1010 relative to base 1002 and relative to the ultrasonic welding horn 604. Motor 1024 may include pneumatic or hydraulic cylinders, as shown, or any other mechanism suitable for selectively raising and/or lowering mounting member 1010 relative to base 1002. In one embodiment, motor 1024 includes a commercially available Allen Bradley servo motor. Control assembly 1020 may further include a second sensor 1024a for providing feedback, which may be used to position anvil member 2602 of active anvil assembly 2600 relative to ultrasonic welding horn 604 (FIG. 4). In particular, second sensor 1024a, may be configured to measure force, torque, distance, and/or other conditions experienced by active anvil assembly 2600. More specifically, second sensor 1024a is configured to provide torque and/or distance feedback to active anvil assembly 2600. Control assembly 1020 may also include one or more ports 1022 for selectively connecting control assembly 1020 with monitoring assembly 2000 (FIG. 2), a command station (not shown), a power source (not shown), and/or any other device or network (not shown).

With reference back to FIG. 6B, trimming assembly 700 is configured to cut tapered surface 17 of looped end portion 10. Trimming assembly 700 includes a trimming blade 702, which may be powered by an ultrasonic horn 704. Trimming assembly 700 further includes a trim gripper 706 for gripping thread 11 as trimming blade 702 engages thread 11. Trim gripper 706 is configured to move laterally or side to side, in the direction of arrows "G," vertically or up and down, in the direction of arrows "H," and front and back, in the direction of arrow "I." Trim blade 702 is also configured to move laterally or side to side, vertically or up and down, and front and back, in the direction of arrows "G," "H," and "I." The speed, path, and frequency at which ultrasonic horn 704 and/or trimming blade 702 move, may be adjusted to affect the configuration of tapered surface 17. Further, trim blade 702 is configured to be advanced and retracted relative to trim gripper 706. In one embodiment, trimming blade 702 is configured to be rotated one-hundred and eighty degrees (180°) about its longitudinal axis such that both cutting surfaces thereof may be used. Although shown adapted for use as an ultrasonic cutter, trimming assembly 700 may be configured cut tapered surface 17 without the use of ultrasonic energy. In an alternate embodiment, a laser may be used to cut tapered surface 17. Alternatively, trimming blade 702 may be heated to assist in the cutting of thread 11.

With reference still to FIG. 6B, trimming assembly 700 further includes a trimming base 710 securely connected with base 1002 of mounting assembly 1000. Base assembly 710 may be operably connected to control assembly 1022, monitoring assembly 2000 (FIG. 2), a command station (not shown), a power source (not shown), and/or any other device or network (not shown).

With reference back to FIG. 4, cutter assembly 800 is configured to cut thread 11 upon completion of the looped end forming process. Cutter assembly 800 includes a cutting blade 802. Cutter assembly 800 is configured to move parallel to initial gripper assembly 300, in the direction of arrows "A". Cutter assembly 800 is configured to cut thread 11 once thread 11 has attained an appropriate length. Cutter assembly 800 may be configured to cut a straight or tapered end on a proximal end 10a (FIG. 1A) of suture 10.

With reference to FIGS. 2 and 4, lengthening assembly 900 is configured to increase the length of thread 11 prior to thread 11 being cut by cutter assembly 800. As shown, lengthening assembly 900 includes a set of fixed rollers 902 and a set of adjustable rollers 904. Although shown including three and two rollers, respectively, sets of fixed and adjustable rollers 902, 904 may include any number of rollers. When thread 11 is received between fixed and adjustable rollers 902, 904, movement of adjustable rollers 904 relative to fixed rollers 902, in the direction of arrows "I", causes thread 11 to lengthen. The greater the number of rollers 902, 904, the less relative movement between rollers 902, 904 is necessary to lengthen thread 11.

Monitoring assembly 2000 is configured to monitor the various steps of the looped end forming process. Monitoring assembly 2000 includes a screen 2002 and a control panel 2004.

The operation of forming station 100 will now be described with reference to 2-6B. Thread 11 extends from spool 202 through first guide member 203 before being received about roller assembly 204. Thread 11 is wrapped around fixed rollers 204a and adjustable rollers 204b of roller assembly 204 four times, and is then received about first and second rollers 205, 206 before being received through second guide member 207. The number of times thread 11 is wrapped around each rollers 204a, 206 may vary depending on the size and/or composition of thread 11.

With continued reference to FIGS. 2-6B, thread 11 extends through second guide member 207 where it is grasped by initial gripper 302 prior to being grasped by rotating gripper 402. Initial grippers 302 then releases thread 11 and flipper gripping assembly 400 translates towards anvil member 2602 of active anvil assembly 2600 as carriage assembly 500 translates towards anvil member 2602 from the opposite direction. Flipper gripping assembly 400 and carriage assembly 500 are configured such that as carriage assembly 500 nears flipper gripping assembly 400, hook 508 of hook assembly 506 is received in the slot (not shown) of mandrel 407. Once hook 508 is received within the slot, rotating gripper 402 rotates, in the direction of arrow "B", to loop thread 11 about mandrel 407. Flipper gripping assembly 400 and carriage assembly 500 then move to position first and second sections 13, 14 of thread 11 within channel 2602a of anvil member 2602. As carriage assembly 500 approximates away from flipper gripping assembly 400, hook 508 extends from within the slot formed in mandrel 407 with thread 11 received thereabout.

In one embodiment, once first and second sections 13, 14 of thread 11 are received with channel 2602a of anvil member 2602, ultrasonic horn 604 is activated and flat die 606 is approximated towards anvil member 2602, in the direction of arrow "E". Engagement of flat welding die 606 with first section 13 of thread 11 causes first and second sections 13, 14 to weld together to form joined segment 15 (FIG. 1B). Alternatively, ultrasonic horn 604 may be positioned relative to anvil member 2602 prior to activating ultrasonic horn 604.

As discussed above with reference to FIGS. 6A and 6B, anvil member 2602 may instead, or additionally, be raised/lowered (arrows "J"), moved laterally (arrows "K") and/or moved front/back (arrows "L"), relative to ultrasonic horn 604 to position anvil member 2602 relative ultrasonic horn 604. Ultrasonic horn 604 may be activated prior to, during or after positioning of anvil member 2602 relative to ultrasonic horn 604. The positioning of anvil member 2602 may be accomplished using any number of methods. In each of the below disclosed methods, movement of anvil member 2602 is determined by the compressive force acting on first and second sections 13, 14 of thread 11 and is not a function of the initial position of ultrasonic horn 604. Additionally, in each of methods, ultrasonic horn 604 is not activated until anvil member 2602 is stationary.

In a first method, anvil member 2602 is moved relative to ultrasonic horn 604 until second sensor 1024a in control assembly 1020 senses a predefined torque value, at which point, the movement of anvil member 2602 is stopped and ultrasonic horn 604 is activated. In a second method, movement of anvil member 2602 stops when a predefined torque value is achieved, and then anvil member 2602 is moved an additional user defined distance. In yet a third method, anvil member 2602 is moved until a force feedback provided by first sensor 2610a of active assembly 2600 achieves a predefined set point, at which point, the movement of anvil member 2602 is stopped and ultrasonic horn 604 is activated. In a fourth method, movement of anvil member 2602 stops when a predefined force value, as measured by first sensor is achieved, and then anvil member 2602 is moved an additional user defined distance. The torque and/or force values and/or the additional user defined distance may vary depending on the size and type of thread being used and/or to effect different weld characteristics.

It is envisioned that ultrasonic horn 604 and anvil member 2602 may be moved simultaneously and/or individually to cause the forming of joined segment 15 and/or to effect the characteristics of joined segment 15 (FIG. 1A). Subsequent joining of first and second sections 13, 14 of thread 11, either or both of anvil member 2602 and ultrasonic horn 604 are approximated away from one another.

Once anvil member 2602 and ultrasonic horn 604 have been repositioned such that anvil member 2602 is spaced from ultrasonic horn 604, tail end gripper 504 of carriage assembly 500 grips a tail end (distal end) of thread 11 and rotating gripper 402 releases thread 11. Carriage assembly 500 then moves to position welded first and second section 13, 14 of thread 11 within gripping anvil 706 of trimming assembly 700. Gripping anvil 706 maintains thread 11 as trimming blade 704 of ultrasonic horn 702 is moved to cut tapered surface 17 (FIG. 1A) into first section 13 of thread 11. Alternatively, and discussed above with reference to FIGS. 6A and 6B, during forming of cut tapered surface 17, gripping anvil 706 may be raised/lowered (arrows "H"), moved laterally (arrows "G"), and/or moved front/back (arrows "I"), relative to trimming blade 702, to affect the characteristics of cut tapered surface 17 (FIG. 1A). Gripping anvil 706 then releases thread 11 and carriage assembly 500 continues to translate away from supply assembly 200 to extend the length of thread 11. It is envisioned that ultrasonic horn 702 and gripping anvil 706 may be moved simultaneously and/or individually to form cut tapered surface 17. Cutting assembly 900 is then activated to cut thread 11. Prior to the cutting of thread 11, tension is applied to loop 12 (FIG. 1A) of thread 11 by the tensioning cylinder (not shown) located within carriage assembly 500 to test the strength of weld 15. Optionally, thread 11 may engage lengthening assembly 800 to extend the length of thread 11 prior to cutting.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that system 100 may include more than one welding assembly 600 and/or trimming assembly 700 to produce more than one suture 10 per activation.

What is claimed is:

1. A system for forming a looped suture, the system comprising:
   a suture supply assembly configured to supply a thread;
   a positioning assembly configured to position a first section of the thread adjacent a second section of the thread to form a loop in the thread; and
   a welding assembly configured to secure the loop in the thread, the welding assembly including an active anvil assembly, the active anvil assembly including, an anvil member;
   a first sensor operably connected to the anvil member, the first sensor configured to provide at least one of force, torque or distance feedback; and
   a control assembly.

2. The system of claim 1, wherein the active anvil assembly includes a mounting member, the control assembly being configured for actuating the mounting member to raise and lower the anvil member in response to feedback provided by the first sensor.

3. The system of claim 2, wherein the anvil member is configured to operate with an ultrasonic welding horn to join the first section of the thread to the second section of the thread to form the loop in the thread.

4. The system of claim 3, wherein the control assembly includes a motor configured to move the mounting member in relation to the ultrasonic welding horn.

5. The system of claim 3, wherein the anvil member is selectively movable in at least first and second directions relative to the ultrasonic welding horn.

6. The system of claim 3, wherein the anvil member is configured to be moved towards and away from the ultrasonic welding horn.

7. The system of claim 1, wherein the anvil member includes a channel configured to selectively receive at least a portion of the first section of the thread.

8. The system of claim 1, wherein the control assembly is configured to move the anvil member vertically.

9. A system for forming a looped suture, the system comprising:
   a welding assembly configured for securing a first length of a thread to a second length of the thread to form a loop in the thread, the welding assembly including:
   an ultrasonic welding horn; and
   an active anvil assembly configured for retaining the first and second lengths of the thread during welding of the loop in the thread, the active anvil assembly including an anvil member and a first sensor connected to the anvil member, the first sensor configured for providing at least one of force, torque or distance feedback.

10. The system of claim 9, wherein the welding assembly further includes a control assembly.

11. The system of claim 10, further including a positioning assembly configured for positioning the first length of the thread adjacent the second length of the thread to form the loop in the thread.

12. The system of claim 10, wherein the active anvil assembly includes a mounting member, the control assembly being configured for actuating the mounting member to raise and lower the anvil member in response to the feedback provided by the first sensor.

13. The system of claim 9, wherein the anvil member is configured to operate with the ultrasonic welding horn to join the first length of the thread and to the second length of the thread to form the loop in the thread.

14. The system of claim 12, wherein the control assembly includes a motor configured to move the mounting member in relation to the ultrasonic welding horn.

15. The system of claim 13, wherein the anvil member is selectively movable in at least first and second directions relative to the ultrasonic welding horn.

16. The system of claim 13, wherein the anvil member is configured to be moved towards and away from the ultrasonic welding horn.

17. The system of claim 9, wherein the anvil member includes a channel configured to selectively receive at least a portion of the first length of the thread.

18. The system of claim 10, wherein the control assembly is configured to move the anvil member vertically.

\* \* \* \* \*